(12) United States Patent
Elizarov et al.

(10) Patent No.: US 7,741,121 B2
(45) Date of Patent: Jun. 22, 2010

(54) SYSTEM FOR PURIFICATION AND ANALYSIS OF RADIOCHEMICAL PRODUCTS YIELDED BY MICROFLUIDIC SYNTHESIS DEVICES

(75) Inventors: Arkadij M Elizarov, Valley Village, CA (US); Hartmuth C. Kolb, Playa Del Rey, CA (US); Jianzhong Zhang, Brea, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 133 days.

(21) Appl. No.: 11/895,636

(22) Filed: Aug. 23, 2007

(65) Prior Publication Data

US 2008/0064110 A1    Mar. 13, 2008

Related U.S. Application Data

(60) Provisional application No. 60/839,908, filed on Aug. 24, 2006.

(51) Int. Cl.
*G01N 23/00* (2006.01)

(52) U.S. Cl. .................. 436/57; 436/161; 137/625; 422/159; 454/121; 536/122

(58) Field of Classification Search .................. None
See application file for complete search history.

(56) References Cited

U.S. PATENT DOCUMENTS

| | | |
|---|---|---|
| 4,536,121 A | 8/1985 | Stewart et al. |
| 5,413,227 A | 5/1995 | Diebold et al. |
| 5,679,580 A | 10/1997 | Ball et al. |
| 5,988,603 A | 11/1999 | McCampbell et al. |
| 6,431,976 B1 | 8/2002 | Auquier |
| 7,144,568 B2 | 12/2006 | Ricard et al. |
| 2008/0064110 A1 | 3/2008 | Elizarov et al. |
| 2008/0281090 A1 | 11/2008 | Lee et al. |
| 2009/0036668 A1 | 2/2009 | Elizarov et al. |
| 2009/0050713 A1 | 2/2009 | Matveev |
| 2009/0095635 A1 | 4/2009 | Elizarov et al. |
| 2009/0118112 A1 | 5/2009 | Ozaki |

FOREIGN PATENT DOCUMENTS

WO    WO 2008/128201    10/2008

OTHER PUBLICATIONS

Miro, Manuel, et al. Solid reactors in sequential injection analysis: ecent trends in the environmental field, 2005, Tends in analytical chemistry, vol. 25(3), pp. 267-281.*

(Continued)

*Primary Examiner*—Yelena G Gakh
*Assistant Examiner*—Robert Xu
(74) *Attorney, Agent, or Firm*—Joshua B. Ryan

(57) ABSTRACT

The present application is generally directed to microfluidic devices and methods for the achievement and assessment of chemical and radiochemical purity of (microfluidic) radio-synthesis products. More particularly, the current application relates to systems for purification and analysis of radiochemical products yielded by microfluidic synthesis devices.

42 Claims, 9 Drawing Sheets

OTHER PUBLICATIONS

Lee, Chung-cheng, et al., Multistep Synthesis of a Radiolabeled Imaging Probe Using Intergrated Microfluidics, 2005, Science, vol. 310, pp. 1793-1796.*

Cobben, David, C.P., et al, 18F-FLT PET for Visualization of Laryngeal Cancer: Comparison with 18F-FDG PET, 2004, The Journal of Nuclear Medicine, vol. 45(2), pp. 226-231.*

Carroll, L. R., et al., Compact, Solid-State Radiation Detectors for Use in PET Isotope and Radio-Chemistry Laboratories, 2003, retrieved from Internet web site: http://web.archive.org/web/20030520224524/http://www.carroll-ramsey.com/detsexp.pdf.*

RSC Publishing; Highlights in Chemical Technology; Instant Insight: Probing radioactive research Apr. 14, 2009; pp. 1-2.

Manuel Miro, Elo Harald Hansen; Trends in Analytical Chemistry, vol. 25, No. 3, 2006; Solid reactors in sequential injection analysis: recent trends in the environmental field; pp. 267-281.

Dr. Mauricio Rostagno; Chemistry Analytical Chemistry; Monolithic columns for fast high-performance liquid chromatography separations; Feb. 14, 2009; pp. 1-4.

David C. P. Cobben, MD, et al.; F-FLT PET for Visualization of Laryngeal Cancer: Comparison with $^{18}$F-FDG PET; The Journal of Nuclear Medicine; vol. 45, No. 2, Feb. 2004; pp. 226-231.

Philip W. Miller; Radiolabelling with short-lived PET (positron emission tomography) isotopes using microfluidic reactors; J. Chem Technol Biotechnol 2009; 84: 309-315; 2008 Society of Chemical Industry.

* cited by examiner

SYSTEM FOR PURIFICATION AND ANALYSIS OF RADIOCHEMICAL PRODUCTS YIELDED BY MICROFLUIDIC SYNTHESIS DEVICES

RELATED APPLICATION

This application claims priority to U.S. Provisional Application No. 60/839,908, filed Aug. 24, 2006, the contents of which are hereby incorporated in their entirety by reference.

FIELD OF THE INVENTION

The current application relates generally to devices and methods for the assessment of chemical and radiochemical purity of radiosynthetic products. More particularly, the current application relates to systems for purification and analysis of radiochemical products yielded by microfluidic synthesis devices.

BACKGROUND OF THE INVENTION

Microfluidic devices can offer a variety of advantages over macroscopic reactors, such as reduced reagent consumption, high surface-to-volume ratios, and improved control over mass and heat transfer. (See, K. Jahnisch, V. Hessel, H. Lowe, M. Baems, *Angew. Chem.* 2004, 116, 410-451; *Angew. Chem. Int. Ed. Engl.* 2004, 43, 406-446; P. Watts, S. J. Haswell, *Chem. Soc. Rev.* 2005, 34, 235-246; and G. Jas, A. Kirschning, *Chem. Eur. J.* 2003, 9, 5708-5723.) A microfluidic device can be integrated with a computer control system in order to perform complicated chemical and biological processes in an automated fashion.

Positron Emission Tomography (PET) is a molecular imaging technology that is increasingly used for detection of disease. PET imaging systems create images based on the distribution of positron-emitting isotopes in the tissue of a patient. The isotopes are typically administered to a patient by injection of probe molecules, which comprise a positron-emitting isotope, e.g. carbon-11, nitrogen-13, oxygen-15, or fluorine-18, attached to a molecule that is readily metabolized or localized in the body or that chemically binds to receptor sites within the body. The short half-lives of the positron emitters require that synthesis, analysis and purification of the probes are completed rapidly.

Single photon emission computed tomography (SPECT) is another nuclear medicine tomographic imaging technique using gamma rays emitted from positron probes. SPECT is able to provide true 3D information. In particular, gated SPECT (timed acquisition) of the heart can be used to obtain quantitative information about myocardial perfusion, thickness, and contractility of the myocardium during various parts of the cardiac cycle. Additionally, SPECT can be used for tumor imaging, infection (leukocyte) imaging, thyroid imaging or bone imaging. Isotopes commonly used in SPECT include technetium-99, iodine-123 and indium-111, which can be attached to a molecule that is readily metabolized or localized in the body or that chemically binds to receptor sites within the body.

Microfluidic devices have been designed and tested for radio-synthesis of radiometric probes. A microfluidic device for the multistep synthesis of a radiolabeled imaging probe has been disclosed in, for example Lee, C-C, et al., *Science* 2005 310:1793-1796; Gillies, J M et al., *Appl Radiat Isot* 2006 64(3):325-32 and 333-336; and Audrain *Angew Chem Int Ed Engl* 2007 46(11):1772-5. Those devices, as well as those disclosed in US 2007-0051412 and US 2004-0258615, are non-exclusive examples of the type synthetic devices that can be used with the systems disclosed herein.

In order for microfluidic devices to be used in clinical applications, the desired products need to be isolated in pure form and their quality has to be precisely analyzed and recorded. Radio-synthesis of probes in microfluidics devices generally yields very small amounts of product in a very small volume of typically aqueous solvent (1-50 µL, even 1-10 µL). It is difficult to analyze and purify these products by conventional methods, without losing the targeted product due to the small sample volumes compared to the volumes and surface area of the vessels and tubing the product encounters en route. When working with smaller sample volumes, product loss from routine handling and required transfers is more significant. Generally users either have accepted the purity and yield achieved by conventional HPLC or run multiple sequential purifications. However, conventional methods do not allow enough precision in the isolation of the desired peaks from HPLC; conventional methods also require manual handling which leads to product losses and introduces errors. Furthermore, the short half-life of many of the radiometric probes requires the development of any new analytical processes to be relatively fast and efficient, that is with relatively short overall processing cycles and high yields. The isolation/detection/collection systems of the present application are complementary to microfluidic radio-synthesis devices, which operate with small volumes.

The systems described in the present application provide small scale, integratable and self-contained units. These systems are substantially isolated from the outside environment, excepting reagent, buffer or sample ports, and are able to perform fluidic operations while maintaining precise control of the amounts of fluids to be delivered. The sealed nature and readily automatable systems also protect fluid operation performed in these devices from contaminating influences from the outside environment, such as chemical or biological contamination, including human error that is generally associated with manual operations, e.g. measurement errors, incorrect reagent additions, detection errors and the like.

SUMMARY OF THE INVENTION

The present application is generally directed to a system comprising a microfluidic device(s) (or chip) that is placed at the exit of an HPLC column and is used for the detection and isolation of a radiolabeled compound. The microfluidic detection/isolation chip is equipped with at least one of a spectrophotometric detector and a radiometric detector and can be attached to a controller that manipulates at least one valve on the chip based on the response of the detector(s) as the fractions are eluted from the column. The precision of the detection and construction of feedback loops between the detector(s), the controller and the valve(s) allow this chip to isolate various products. This system is designed as an efficient product isolation system complementary to "coin-shaped reactor" radio-synthesis devices familiar to those of skill in the art.

The systems disclosed herein provide a single, continuous path from synthesis device to HPLC column to detection/isolation device without requiring intermediate steps, such as the collection of the reaction mixture in a sample loop or its fixed volume equivalent. In one embodiment, the system is automated and self-contained and is able to detect and isolate desired products, which can then be transferred from the system in a purified injectable form. In another embodiment the systems disclosed herein feature an automated in-line purification and isolation of a radiolabeled compound, providing high purification efficiency, low sample loss and integrated sample concentration/solvent removal. Yet another embodiment disclosed herein is a system comprising a microfluidic radio-synthesis device, an HPLC column, and a detection/isolation device; further disclosed is a method of using such a device in the synthesis, purification and isolation of a radiolabeled compound.

Embodiments, Aspects and Variations of the Present Application

The present application provides the following embodiments, aspects and variations:

In one embodiment, the present application is directed to a system for the analysis and/or purification of a radiolabeled compound comprising: i) a microfluidic analytical device; ii) at least one radiometric detector coupled to the top or the bottom of the analytical device; and iii) a high pressure liquid chromatography (HPLC) column in fluid communication with the analytical device; wherein the system is coupled to a microfluidic radio-synthesis device and the HPLC column operates independently of sample volume received from the radio-synthesis device; In one aspect, the analytical device further comprises at least one valve; and the system further comprises at least one controller, which is operatively attached to at least one of the spectrophotometric detector and the radiometric detector, receives a signal from at least one of detectors, and controls the operation of the at least one valve to isolate one or more radiolabeled compounds. In another aspect, the HPLC column is in direct fluid communication with a check valve, which is in fluid communication with at least one solvent pump and with the radio-synthesis device; and the radiolabeled compound prepared in the radio-synthesis device is passed through the check valve to the HPLC column.

In another embodiment, the present application is directed to a system for the analysis and/or purification of a radiolabeled compound comprising:

i) a microfluidic analytical device having a top and a bottom and comprising:
  a) a network of flow channels;
  b) an inlet port;
  c) a fraction outlet port; and
  d) a waste outlet port;
ii) a spectrophotometric source using a UV, visible or near IR light source;
iii) a spectrophotometric detector, wherein the spectrophotometric source and the spectrophotometric detector are each attached to the analytical device via a fiber optic cable;
iv) at least one radiometric detector coupled to the top or the bottom of the analytical device; and
v) a high pressure liquid chromatography (HPLC) column in fluid communication with the analytical device, wherein the system is coupled to a microfluidic radio-synthesis device and the HPLC column operates independently of sample volume received from the radio-synthesis device.

In one aspect of any of the disclosed devices, each of the analytical device and the radiometric detector is substantially shielded from the radio-synthesis device and the HPLC column by a radiation shield. In another aspect, the analytical device further comprises at least one valve; and the system further comprises at least one controller, which is operatively attached to at least one of the spectrophotometric detector and the radiometric detector, receives a signal from at least one of detectors, and controls the operation of at least one valve on the analytic device to isolate one or more radiolabeled compounds.

In one aspect, the spectrophotometric source is a source of UV light and the spectrophotometric detector detects UV light. In another aspect, a first radiometric detector is attached to the top of the analytical device, a second radiometric detector is attached to the bottom of the analytical device, and the first and second radiometric detectors are both operatively attached to the controller.

In one aspect, the HPLC column is in fluid communication with at least one solvent pump via a flow channel. In another aspect, the HPLC column is in direct fluid communication with a check valve which is further in fluid communication with the solvent pump. In yet another aspect, the check valve is also in fluid communication with the radio-synthesis device, and the radiolabeled compound prepared in the radio-synthesis device is passed through the check valve to the HPLC column. In one variation, the radio-synthesis device is rinsed with solvent from hardware related to the synthesis device, such as, for example a syringe pump; the rinse volume is then transferred from the HPLC column via the flow channel.

In one aspect of any of the disclosed devices, at least one solvent pump is in fluid communication with a solvent source for solvent (A) and is adapted to transfer solvent (A) from the solvent source to the HPLC column. As used herein, a solvent pump is described as being in fluid communication with a solvent source, for example, means that the solvent pump is configured such that it allows a fluid, such as a solvent, to flow, with or without intermediate elements or devices, such as valves, pumps, and the like, from the source of the solvent, such as a reservoir, to the solvent pump. In another aspect, at least one solvent pump is in fluid communication with at least one solvent source for solvent (A) and at least one solvent source for solvent (B); and the solvent pump is configured to transfer from the solvent source to the HPLC column one or more of solvent (A) solvent (B) and a mixture of solvent (A) and solvent (B). In yet another aspect, a first solvent pump is in fluid communication with at least one solvent source for solvent (A) and is adapted to transfer solvent (A) from the solvent source to the HPLC column and a second solvent pump is in fluid communication with at least one solvent source for solvent (B) and is adapted to transfer solvent (B) from the solvent source to the HPLC column. In still another aspect, solvent (A) is an aqueous solvent and solvent (B) is an organic solvent.

In one aspect of any of the devices or systems disclosed herein, the radiolabeled compound is a positron emission tomography (PET) imaging agent or a single photon emission computed tomography (SPECT) imaging agent. In another aspect, the radiolabeled compound contains a label selected from the group consisting of carbon-11, fluorine-18, nitrogen-13, oxygen-15, technetium-99, iodine-123 and indium-111. In a particular example the radiolabeled compound contains fluorine-18. Such compounds include compounds selected from a group consisting of $^{18}$F-FLT ([$^{18}$F]fluorothymidine), $^{18}$F-FDDNP (2-(1-{6-[(2-[F$^{18}$]fluoroethyl)(methyl)amino]-2-naphthyl}ethylidene)-malonitrile), $^{18}$F-FHBG (9-[4-[$^{18}$F]fluoro-3-(hydroxymethyl)butyl]guanine or [$^{18}$F]-penciclovir), $^{18}$F-FESP ([$^{18}$F]-fluoroethylspiperone), $^{18}$F-p-MPPF (4-(2-methoxyphenyl)-1-[2-(N-2-pyridinyl)-p-[$^{18}$F]fluorobenzamido]ethylpiperazine) and $^{18}$F-FDG ([$^{18}$F]-2-deoxy-2-fluoro-D-glucose). In particular, the radiolabeled compound is $^{18}$F-FLT. In one aspect, after purification, $^{18}$F-FLT is greater than about 95% pure. In another aspect, after purification, $^{18}$F-FLT is greater than about 96% pure. In one aspect, the radiolabeled compound is obtained in a pharmaceutically acceptable formulation; in one variation the radiolabeled compound is obtained in an aqueous injectable pharmaceutically acceptable formulation.

In one aspect of any of the disclosed devices, the output volume of the analytical device is between about 5 µL and about 5 mL. Generally, the output volume of the analytical device is between about 100 µL and about 2 mL; alternately, the output volume is between about 200 µL and about 1.5 mL. Usually, the lower limit of the output volume is about 50, 100, 200, or 400 µL; usually the upper limit of the output volume is about 750 µL, 1 mL, 1.5 mL, 2 mL or 4 mL. In one aspect, the reaction volume of a radio-synthesis chip ranges from about 5 µL to about 40 µL and is usually between about 10 µL and about 25 µL. In one aspect, the rinse volume from a radio-synthesis chip can range from about 5 µL to about 5 mL. Usually, the rinse volume is between about 10 µL and about 200 µL. Alternately, the rinse volume can range from about 15 µL to about 175 µL, or from about 25 µL to about 150 µL. The lower limit of the rinse volume can be about 10, 25, 50, 100 or 250 µL; usually the upper limit of the rinse volume is about 750 µL, 1 mL, 1.5 mL, 2 mL or 4 mL. For each of the microfluidic devices, while an upper limit of about 5 mL is generally identified, the system described is configured to handle greater volumes, such as for example rinse volumes of about 10 mL or an output from the analytical device of about 10 mL. In one aspect, analytical device is in fluid communication with a fraction collector via a flow channel. In another aspect, the fraction collector is equipped with a solvent removal system. In yet another aspect, the fraction collector is in fluid communication with a secondary analytical system comprising a mechanism for removing at least one microliter aliquot from the fraction collector.

One embodiment of the present application is a system for the analysis and/or purification of a $^{18}$F-labeled compound comprising:
  i) a microfluidic analytical device having a top and a bottom and comprising:
    a) a network of flow channels;
    b) an inlet port;
    c) a fraction outlet port; and
    d) a waste outlet port;
  ii) a UV light source;
  iii) a UV detector, wherein the UV light source and the UV detector are each attached to the analytical device via a fiber optic cable;
  iv) one radiometric detector coupled to the top of the analytical device;
  v) a second radiometric detector coupled to the bottom of the analytical device; and
  vi) a high pressure liquid chromatography (HPLC) column in fluid communication with the analytical device; wherein the system is coupled to a microfluidic radio-synthesis device and the HPLC column operates independently of sample volume received from the radio-synthesis device.

Another embodiment of the present application is a method for the analysis and/or purification of a radiolabeled compound comprising providing reactants to a microfluidic radio-synthesis device and analyzing and/or purifying the radiolabeled compound synthesized in the microfluidic radio-synthesis device comprising use of a system comprising: a) a microfluidic analytical device; b) at least one radiometric detector coupled to the top or the bottom of the analytical device; and c) a high pressure liquid chromatography (HPLC) column in fluid communication with the analytical device; wherein the system is coupled to the microfluidic radio-synthesis device and the HPLC column operates independently of sample volume received from the radio-synthesis device. In one aspect, the analytical device further comprises at least one valve; and the system further comprises at least one controller, which is operatively attached to at least one of the spectrophotometric detector and the radiometric detector, receives a signal from at least one of detectors, and controls the operation of the at least one valve to isolate one or more radiolabeled compounds. In another aspect, the HPLC column is in direct fluid communication with a check valve, which is in fluid communication with at least one solvent pump and with the radio-synthesis device; and the radiolabeled compound prepared in the radio-synthesis device is passed through the check valve to the HPLC column.

Yet another embodiment of the present application is a method for the analysis and/or purification of a radiolabeled compound comprising providing reactants to a microfluidic radio-synthesis device and analyzing and/or purifying the radiolabeled compound synthesized in the microfluidic radio-synthesis device comprising use of a system comprising:
  a) a microfluidic analytical device having a top and a bottom and comprising:
    A) a network of flow channels;
    B) an inlet port;
    C) a fraction outlet port; and
    D) a waste outlet port;
  b) a spectrophotometric source using a UV, visible or near IR light source;
  c) a spectrophotometric detector, wherein the spectrophotometric source and the spectrophotometric detector are each attached to the analytical device via a fiber optic cable;
  d) at least one radiometric detector coupled to the top or the bottom of the analytical device; and
  e) a high pressure liquid chromatography (HPLC) column in fluid communication with the analytical device; wherein the system is coupled to the microfluidic radio-synthesis device and the HPLC column operates independently of sample-volume received from the radio-synthesis device.

In one aspect of the any of the methods disclosed herein, each of the analytical device and the radiometric detector is substantially shielded from the radio-synthesis device and the HPLC column by a radiation shield. In another aspect, the analytical device further comprises at least one valve and the system further comprises at least one controller, which is operatively attached to at least one of the spectrophotometric detector and the radiometric detector, receives a signal from at least one of the detectors, and controls the operation of the valve on the analytical device to isolate one or more radiolabeled compounds. In one aspect of any of the methods disclosed herein, the spectrophotometric source is a source of UV light and the spectrophotometric detector detects UV light. In one aspect, a first radiometric detector is attached to the top of the analytical device, a second radiometric detector is attached to the bottom of the analytical device, the first and second radiometric detectors are both operatively attached to the controller, and any radiation signal not simultaneously received by both detectors is excluded from processing.

In one aspect, the HPLC column is in fluid communication with at least one solvent pump via a flow channel. In one variation, the HPLC column is in direct fluid communication with a check valve which is further in fluid communication with the one solvent pump. In another variation, the check valve is also in fluid communication with the radio-synthesis device, and the radiolabeled compound prepared in the radio-synthesis device is passed through the check valve to the HPLC column. In yet another variation, the radio-synthesis device is rinsed with solvent from hardware related to the synthesis device, such as, for example a syringe pump; the rinse volume is then transferred from the HPLC column via the flow channel.

In one aspect of any of the methods disclosed herein, at least one solvent pump is in fluid communication with a solvent source for solvent (A) and is adapted to transfer solvent (A) from the solvent source to the HPLC column. In another aspect, at least one solvent pump is in fluid communication with at least one solvent source for solvent (A) and at least one solvent source for solvent (B); the solvent pump is configured to transfer from the solvent source to the HPLC column one or more of: solvent (A), solvent (B), and a mixture of solvent (A) and solvent (B). In yet another aspect, a first solvent pump is in fluid communication with at least one solvent source for solvent (A) and is adapted to transfer solvent (A) from the solvent source to the HPLC column and a second solvent pump is in fluid communication with at least one solvent source for solvent (B) and is adapted to transfer solvent (B) from the solvent source to the HPLC column. In one variation solvent (A) is an aqueous solvent and solvent (B) is an organic solvent. In another variation, passage of solvent (A) through the HPLC column removes one or more hydrophilic impurities. In one aspect, the one or more hydrophilic impurities include $^{18}$F-ions.

In one aspect of any of the methods disclosed herein, the radiolabeled compound is a positron emission tomography (PET) imaging agent or a single photon emission computed tomography (SPECT) imaging agent.

In one aspect of any of the disclosed methods, the radiolabeled compound is a positron emission tomography (PET) imaging agent or a single photon emission computed tomography (SPECT) imaging agent. In another aspect, the radiolabeled compound contains a label selected from the group consisting of carbon-11, fluorine-18, nitrogen-13, oxygen-15, technetium-99, iodine-123 and indium-111. In a particular example, the radiolabeled compound contains fluorine-18. Such compounds include compounds selected from a group consisting of $^{18}$F-FLT ([$^{18}$F]fluorothymidine), $^{18}$F-FDDNP (2-(1-{6-[(2-[F-$^{18}$]fluoroethyl)(methyl)amino]-2-naphthyl}ethylidene)malononitrile), $^{18}$F-FHBG (9-[4-[$^{18}$F]fluoro-3-(hydroxymethyl)butyl]guanine or [$^{18}$F]-penciclovir), $^{18}$F-FESP ([$^{18}$F]-fluoroethylspiperone), $^{18}$F-p-MPPF (4-(2-methoxyphenyl)-1-[2-(N-2-pyridinyl)-p-[$^{18}$F]fluorobenzamido]ethylpiperazine) and $^{18}$F-FDG ([$^{18}$F]-2-deoxy-2-fluoro-D-glucose). In particular, the radiolabeled compound is $^{18}$F-FLT. In one aspect, after purification, $^{18}$F-FLT is greater than about 95% pure. In another aspect, after purification, $^{18}$F-FLT is greater than about 96% pure. In one aspect, the radiolabeled compound is obtained in a pharmaceutically acceptable formulation; in one variation the radiolabeled compound is obtained in an aqueous injectable pharmaceutically acceptable formulation.

In one aspect of any of the disclosed devices, the output volume of the analytical device is between about 5 μL and about 5 mL. Generally, the output volume of the analytical devices is between about 100 μL and about 2 mL; alternately, the output volume is between about 200 μL and about 1.5 mL. Usually, the lower limit of the output volume is about 50, 100, 200 or 400 μL; usually the upper limit of the output volume is about 750 μL, 1 mL, 1.5 mL, 2 mL or 4 mL. In one aspect, the reaction volume of a radio-synthesis chip ranges from about 5 μL to about 40 μL and is usually between about 10 μL and about 25 μL. In one aspect, the rinse volume from a radio-synthesis chip can range from about 5 μL to about 5 mL.

Usually, the rinse volume is between about 10 μL and about 200 μL. Alternately, the rinse volume can range from about 15 μL to about 175 μL, or from about 25 μL to about 150 μL. The lower limit of the rinse volume can be about 10, 25, 50, 100 or 250 μL; usually the upper limit of the rinse volume is about 750 μL, 1 mL, 1.5 mL, 2 mL or 4 mL. For each of the microfluidic devices, while an upper limit of about 5 mL is generally identified, the system described is configured to handle greater volumes, such as for example rinse volumes of about 10 mL or an output from the analytical device of about 10 mL. In another aspect, the analytical device is in fluid communication with a fraction collector via a flow channel. In yet another aspect, the fraction collector is equipped with a solvent removal system. In still another aspect, the fraction collector is in fluid communication with a secondary analytical system comprising a mechanism for removing at least one microliter aliquot from the fraction collector.

Yet another embodiment of the present application is a method for the analysis and/or purification of an $^{18}$F-labeled compound comprising providing reactants to a microfluidic radio-synthesis device and analyzing and/or purifying the radiolabeled compound synthesized in the microfluidic radio-synthesis device comprising use of a system comprising:

a) a microfluidic analytical device having a top and a bottom and comprising:
   A) a network of flow channels;
   B) an inlet port;
   C) a fraction outlet port; and
   D) a waste outlet port;
b) a UV light source;
c) a UV detector, wherein the UV light source and the UV detector are each attached to the analytical device via a fiber optic cable;
d) one radiometric detector coupled to the top of the analytical device;
e) a second radiometric detector coupled to the bottom of the analytical device; and
f) a high pressure liquid chromatography (HPLC) column in fluid communication with the analytical device; wherein the system is coupled to the microfluidic radio-synthesis device and the HPLC column operates independently of sample volume received from the radio-synthesis device.

The systems disclosed in the present application work well with very small sample or reaction volumes, since each uses a very small, (almost) dead-volume free flow cell plumbed with microchannels and closely positioned valves. The internal volume of the detection/isolation chip is in the range of about 1 to about 10 μL. This set-up minimizes sample losses as well as inadvertent sample mixing, which is unavoidable in the macroscopic systems used previously. Further the current configuration reduces contamination of the desired fraction eluted from the HPLC with neighboring fractions, due to the increased precision of the sample detection and collection.

DETAILED DESCRIPTION

Definitions

Figure 1:
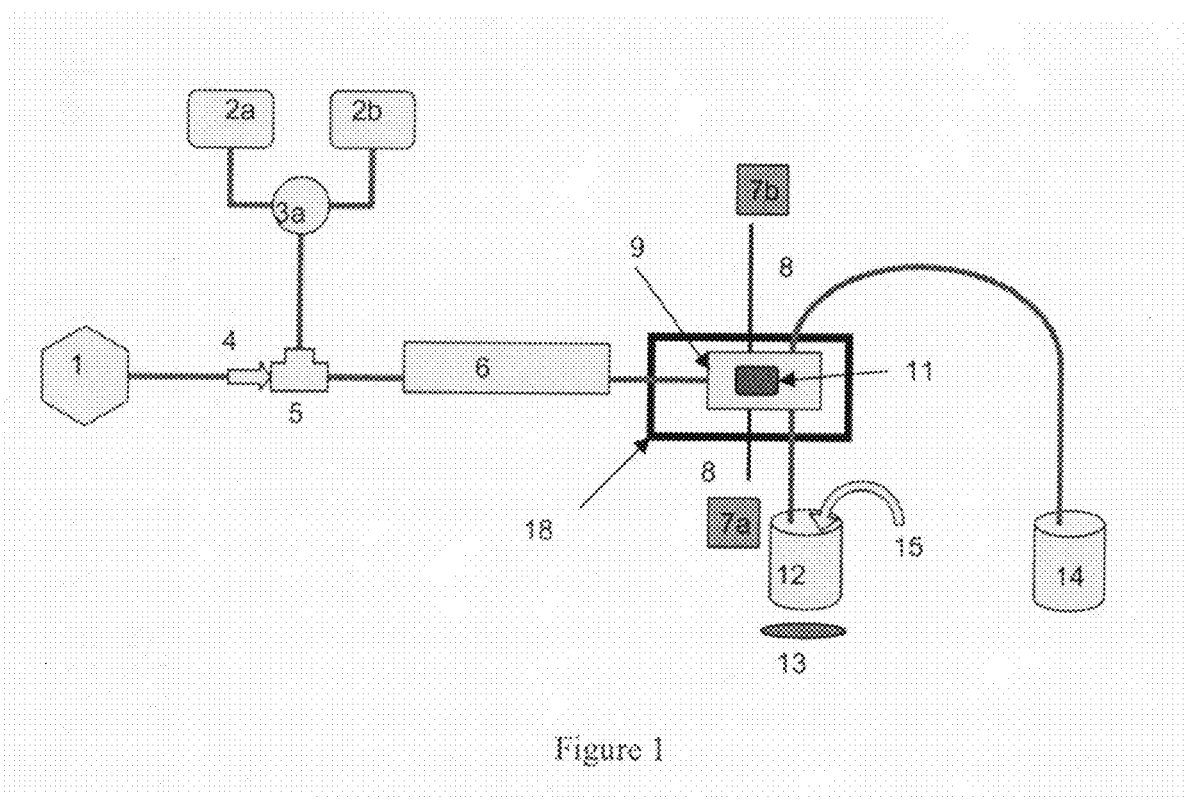
FIG. 1 is a schematic illustration of a system according to one embodiment of the present application in which the microfluidic radio-synthesis device is coupled via a flow channel containing a check valve to an HPLC column. The eluent of the HPLC column is then transferred to a microfluidic detection/isolation module (also referred to herein as 'analytical device') which is equipped to detect the presence of the HPLC fractions and isolate the targeted fraction.

Unless defined otherwise, all technical and scientific terms used herein have the same meanings as commonly understood by one of skill in the art to which this application belongs. Particular methods, devices and materials are described, although any methods, devices and materials similar or equivalent to those described herein can be used in the practice or testing of the present invention.

As used herein, "microfluidic" refers to structures or devices having at least one dimension less than about 500 microns through which one or more fluids are capable of being passed or directed.

A "microfluidic device" is a structure or unit that permits the manipulation and transfer of microliters or nanoliters of liquid into a substrate comprising flow channels, ports and the like. The structure may be constructed using micro-electro-mechanical fabrication methods as known in the art. Examples of such substrates for forming the device include glass, quartz or polymer. Such polymers may include PMMA (polymethylmethacrylate), PC (polycarbonate), PDMS (polydimethylsiloxane) and the like. Such devices may further comprise valves. Components of the system in contact with the radiolabeled sample and related impurities may be realized in a number of materials or their combinations; examples of such materials include poly(etheretherketone) (PEEK), TEFLON, polydicyclopentadiene (pDCPD), and glass.

A "microfluidic radio-synthesis device" or "synthesis device" refers to a microfluidic chip configured for the synthesis of a radiolabeled compound.

A "spectrophotometric source" as described herein is a source of light in the ultraviolet, visible or near IR range. A spectrophotometric source is generally attached to the detection/isolation module via a fiber optic cable or its equivalent.

A "spectrophotometric detector" as described herein is a detector that can detect in the ultraviolet, visible or near IR range. A spectrophotometric detector is generally attached to the detection/isolation module via a fiber optic cable or its equivalent.

As used herein, a "flow channel" refers to a channel (in any form, including a closed channel, a capillary, a trench, groove or the like) on or in a microfluidic substrate (a chip, bed, wafer, laminate or the like having microfluidic channels) through which components are transported. As known in the art, such channels may have a cross section of less than about 1 mm, less than about 0.5 mm, less than about 0.3 mm or less than about 0.1 mm. The flow channels of the present application may also have a cross sectional dimension of between about 0.05 µm and about 1,000 µm, or 0.5 µm to about 500 µm or about 10 µm to about 300 µm. The particular shape and size of the flow channels will depend on the particular application required, including desired throughput and may be configured and sized accordingly.

As used herein, "pharmaceutically acceptable" means a non-toxic material that does not interfere with the effectiveness of the biological and radiochemical activity of the radiolabeled compound(s). Pharmaceutically acceptable includes a material, composition or carrier, such as a liquid diluent, excipient, or solvent that is involved in carrying or transporting the radiolabeled compound(s) and is 'acceptable' in the sense of being compatible with the other ingredients of the formulation and not injurious to the patient. Pharmaceutically acceptable solvents, including water, are well known to those of skill in the art.

The term "hydrophilic" when used in reference to compounds refers to compounds have an affinity for water, e.g. readily absorbing or dissolving in water.

As used herein, "secondary analytical system" refers to a system comprising a mechanism for removing at least one aliquot from the fraction collector. The secondary analytical system can include a mechanism for radiometric and/or spectrophotometric detection, such as those described herein. A secondary analytical system may contain one or more valves, but such valves are not required for the successful operation of the system.

As used herein, "aliquot" refers to a small measurable amount of a solution that is characteristic of the entire solution. An aliquot generally refers to a volume of sample that is to be subjected to a particular manipulation or analysis.

As used herein, "purification" refers to reducing, in the sample of radiolabeled compound, the presence of impurities. Non-exclusive examples of impurities include unconjugated radiolabel, compounds not containing a radiolabel, radiolabeled by-products, and other side products exiting the radio-synthesis device in solution with the targeted radiolabeled compound. In the synthesis of $^{18}$F-FLT, impurities include unconjugated $^{18}$F-ions and unlabeled 3'-deoxy-3'-fluorothymidine. Generally the systems described herein generate samples of radiolabeled compound that are at least 90% pure, alternately at least 95% pure, 96% pure or even 99% pure. Purity of the radiolabeled compound can be determined by methods known to those of skill in the art. Non-exclusive examples of these methods include radiometric and spectrophotometric detection, as well as thin-layer chromatography with radiometric detection (radio-TLC). Purity does not refer to the presence or type of solvent contained in the sample.

As used herein, a "solvent removal system" refers to a system configured to remove solvent from a sample. Such a system can include a source of an inert gas, such as nitrogen, an inlet port for the gas and an outlet port for the combination of gas and vaporized solvent. Alternately, such a system can include a heating source and an outlet port for the vaporized solvent. In another alternative, such a system can comprise use of both an inert gas and a heating source. A solvent removal system can be used to remove a fraction of the solvent present in a sample or alternately, can be used to remove substantially all of the solvent present in a sample. When substantially all of a solvent, such as an organic solvent, is removed from a sample, any organic solvent remaining in the sample is of a low enough amount or concentration that the sample would be considered 'pharmaceutically acceptable.'

As used herein, "collection chip" or "collection device" refers to a microfluidic chip configured for the collection of a sample, where the sample may be transferred from a detection chip.

As used herein, "detection device," or "detection chip" each refers to a microfluidic chip configured for the detection of radiometric and/or spectrophotometric signals of a sample. Such a sample may be eluted directly from an HPLC column or may be transferred from a separately configured collection chip. A detection device may contain one or more valves, but such valves are not required for the successful operation of the device.

As used herein, "detection/isolation chip," "detection/isolation module," "analytical device" or "analytical chip" refers to a microfluidic device configured for both the detection and isolation of a sample. Generally a sample is eluted from an HPLC column onto the chip, which is equipped with flow channels and at least one valve and is attached to at least one of a radiometric and spectrophotometric detector.

As used herein, "sample volume" refers to the volume of the sample transferred to the HPLC column. In this context, the sample volume includes the reaction volume transferred from the radio-synthesis device. The sample volume can also include the rinse volume transferred after rinsing the radio-synthesis device with additional solvent. In one aspect, the reaction volume of a radio-synthesis chip ranges from about 5 µL to about 40 µL and is usually between about 10 µL and about 25 µL. In another aspect, the rinse volume from a radio-synthesis chip can range from about 5 µL to about 5 mL. Usually, the rinse volume is between about 10 µL and about 200 µL. Alternately, the rinse volume can range from about 15 µL to about 175 µL, or from about 25 µL to about 150 µL. The lower limit of the rinse volume can be about 10, 25, 50, 100 or 250 µL; usually the upper limit of the rinse volume is about 750 µL, 1 mL, 1.5 mL, 2 mL or 4 mL. The volume that can be transferred from the synthesis device to the HPLC column is generally within the ranges identified, but the system is configured to handle greater volumes, such as for example, rinse volumes of about 10 mL.

A microfluidic "valve," as used herein, means a device that may be controlled or actuated to control or regulate fluid or solution flow among various components of the microfluidic device, including flow between flow channels, columns, devices and the like. Such valves are known in the art and include, for example, mechanical (or micromechanical valves), (pressure activated) elastomeric valves, pneumatic valves, solid state valves, etc. Examples of such valves and their method of fabrication may be found for example in Felton, "The New Generation of Microvalves" *Analytical Chemistry* 2003 429-432. Non-exclusive examples of valves appropriate for use in the systems presently disclosed include check valves and plunger (piston) valves.

As disclosed herein, a number of different HPLC columns may be employed in the analytical/purification systems disclosed herein. Such columns may include, but are not limited to, monolith columns, open tubular capillary columns ("OTC columns"), and packed capillary columns ("PCLC columns"). Monoliths are blocks of continuous materials made of highly porous rods with two types of pore structures (macropores and mesopores of different sizes), which allow the use of higher flow rates and thus reduce analysis time. Generally, there are four types of monolith capillary columns: particle fixed, silica based, polymer based and molecular imprinted monolith. The monolith columns described below generally are prepared by in situ polymerization of monomeric precursors rather than bead packing. Such columns include, for example, Onyx monolith columns sold by Phenomenex (Torrance, Calif.). In OTC columns, the capillary wall is coated with a highly permeable porous material that serves as the stationary phase. PCLC columns are made by loading the capillary column with silica-modified particles; the small sized particles provide nano-liquid chromatography systems with high efficiency, resolution, selectivity and short analysis time. Direct loading from the microfluidic radio-synthesis device is enabled, as appropriate, by selection of a column, such as a monolith column, which yields lower back pressure.

As described in certain embodiments of the present application, the HPLC column is described to operate "independently" of the sample volume. An HPLC column can be considered to operate independently of sample volume when the reaction mixture sample is loaded onto the column directly from the microfluidic radio-synthesis chip, optionally with a rinse volume, without a sample loop or its fixed volume equivalent and the column efficiently and effectively separates the radiolabeled compound from impurities regardless of the sample size transferred from the radio-synthesis device. The transfer from a batch synthesis device to a batch purification system employed in the systems disclosed herein is unique from systems which employ continuous synthesis in combination with batch purification. In those systems, the output from the synthetic process needs to be collected, for example in a sample loop, before performing the batch purification. The HPLC columns employed in the systems described herein are millimeter scale and can easily purify any practical volume of solution transferred from the microfluidic radio-synthesis device.

FIG. 1 outlines the architecture of a system capable of the synthesis, detection and isolation of radiolabeled products. In this arrangement, the microfluidic radio-synthesis chip, 1, serves an injector of the sample volume onto the HPLC column, 6. Further in this arrangement, the microfluidic analytical device ("detection/isolation module"), 9, follows directly after the HPLC column, 6, and directs its output to one or more fraction collectors, 12, or waste, 14. The flow channel connecting the radio-synthesis chip, 1, to the HPLC column, 6, contains a check valve, 4, and a tee, 5, which itself is further connected to a valve, 3a, attached to solvent sources, 2a and 2b, each of which may further comprise a solvent pump. Each of the spectrophotometric source, 7a, and spectrophotometric detector, 7b, is attached to the analytical device, 9, via a fiber optic cable, 8.

The radiometric detector, 11, of the analytical device, 9, is most effective when shielded from all other sources of radiation by a complete enclosure with appropriate material (e.g. lead, tungsten, or compounds or amalgams of these and other elements). These other sources of radiation include, but are not limited to, the radio-synthesis chip, 1, the HPLC column, 6, the fraction collector, 12, and the waste collector, 14. The radiation shield, 18, may be in flush contact with the detection/isolation module, 9; alternately, the radiation shield, 18, surrounds, but does not touch the module, 9. The fraction collector, 12, is equipped with an inlet port for inert gas, 15. A heating source, 13, can also be applied to the fraction collector, 12.

Figure 2:
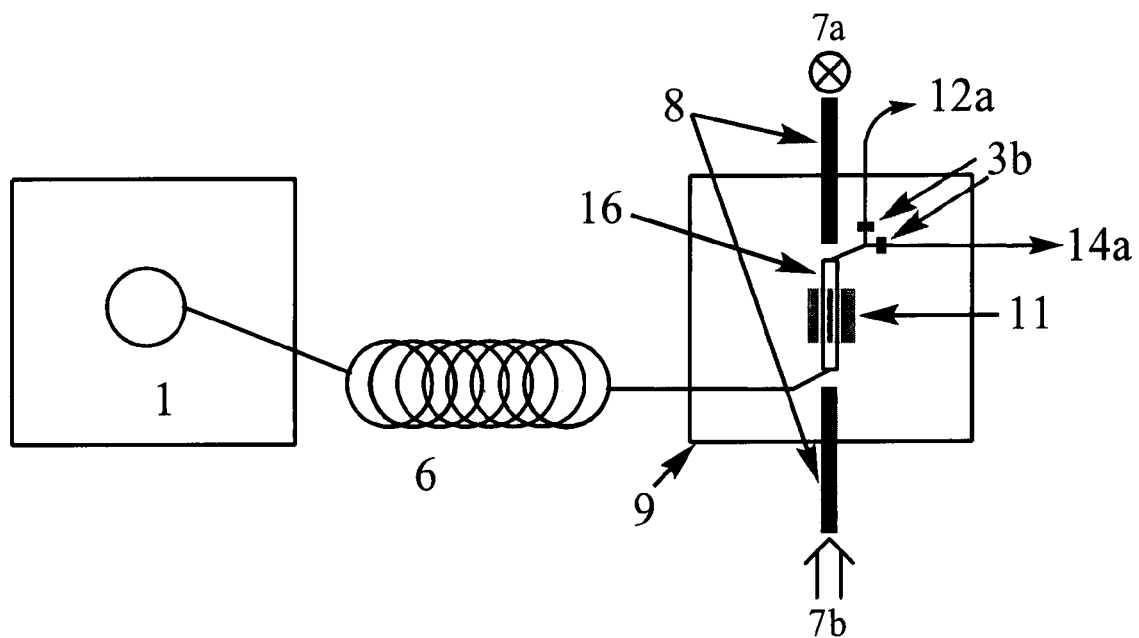
FIG. 2 is a schematic illustration of a system according to one embodiment disclosed in the present application in which the microfluidic analytical device follows an HPLC column, which can be attached to a microfluidic radio-synthesis device. The UV source and UV detector are attached to the analytical device via fiber optics. The radiation detector(s) is positioned either above or below the device or both above and below the device.

FIG. 2 exemplifies an alternate embodiment of the present application. The radio-synthesis chip, 1, is attached to an HPLC column, 6, which in turn is attached to an analytical device, 9. The radiometric detector, 11, is located in close proximity to or is in contact with the flow cell, 16. Each of the spectrophotometric source, 7a, and spectrophotometric detector, 7b, is attached to the analytical device, 9, via a fiber optic cable, 8. The disclosed valves, 3b, control the passage of the solution to the fraction collection, 12a, or to waste, 14a.

In one embodiment of the present application, a signal from the radiometric detector is sent to a controller, which triggers the product fraction collection in the analytical device. The signal originates from the radioactive label, e.g. $^{18}$F, which decays by emitting a positron. The positron in turn produces a pair of gamma photons moving in almost opposite directions. The radiometric detector can be positioned on the top or the bottom of the analytical device. More efficiently, a radiometric detector can be positioned on each of the top and the bottom of the analytical device; in such an arrangement increased sensitivity is derived from real time data processing in which any signal that is not registered simultaneously by both detectors is filtered out. In this way, additional radiometric noise is removed from the analysis. Generally, the radiation detector(s) is attached to the analytical device, but is removable. Appropriate modes of attachment include clamps, screws or even glue; gluing the detector to the analytical device may be most appropriate when the radiometric detector does not need to be removed.

In one embodiment of the present application, the sample size of the isolated radiolabeled compound is at least 250 µCi; generally the sample is about 10 mCi. Alternately, the sample size of the isolated radiolabeled compound is at least 100 mCi, at least 200 mCi or at least 300 mCi. In one variation, the system disclosed herein is configured for isolating at least 1 human dose of the radiolabeled compound in a single 10 minute process cycle; in another variation, at least 10 human doses are isolated in a single 10 minute process cycle; in still another variation, at least 30 human doses are isolated in a single 10 minute process cycle.

The reaction volume of a radio-synthesis chip can range from about 5 µL to about 40 µL and is usually between about 10 µL and about 25 µL. In one aspect, the rinse volume from a radio-synthesis chip can range from about 5 µL to about 5 mL. Usually, the rinse volume is between about 10 µL and about 200 µL. Alternately, the rinse volume can range from about 15 µL to about 175 µL, or from about 25 µL to about 150 µL. The expected volume of the product-containing fraction after HPLC purification is generally between about 100 µL and about 1 mL. The small (approximately 1 µL) volume of the flow cell of the detection/isolation module, which analyses the sample stream, or small portions thereof, allows more precise detection of the beginning and the end of the desired product-containing fraction than flow cells in macroscopic detectors. This improved detection results directly in an increase in the purity of isolated product compared to purity achieved using conventional means.

Figure 3A:
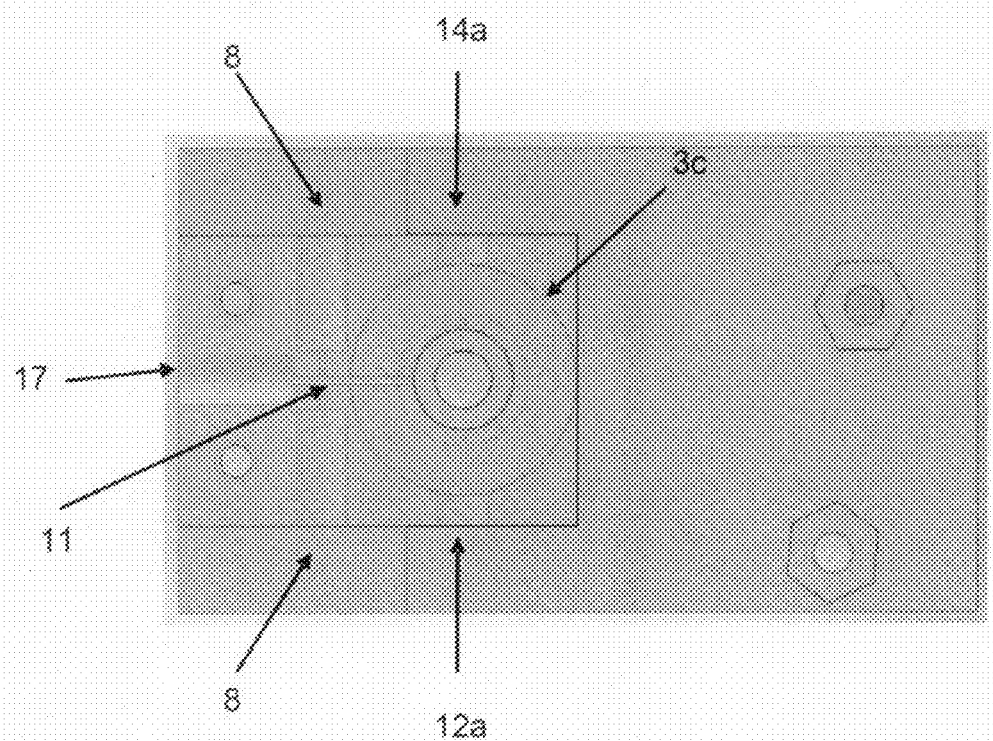
FIG. 3A is a top view of a SolidWorks drawing according to one embodiment of the present application of a microfluidic analytical device configured to direct the fractions eluted from the HPLC column to either waste or fraction collector(s) based on the response measured by the radiometric and/or spectrophotometric detector(s).
Figure 3B:
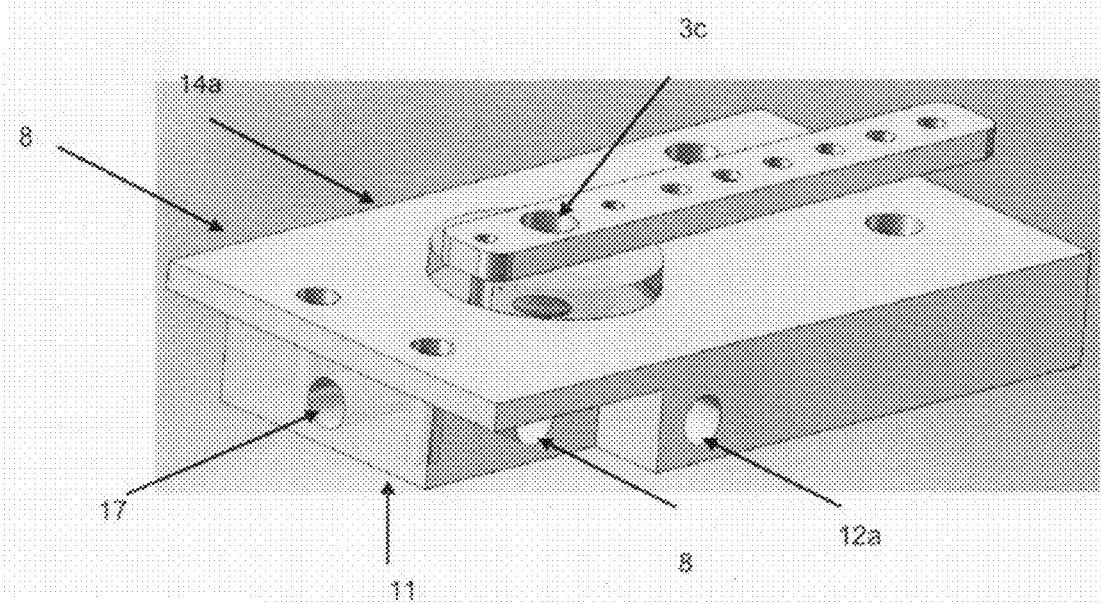
FIG. 3B is an isometric view of a same SolidWorks drawing of the microfluidic analytical device in FIG. 3A.

In one embodiment of the present application, once the product signal(s) is detected, the controller automatically operates the valve(s) to isolate the product fraction. As shown in FIGS. 3A and 3B, the eluent from the HPLC column enters the flow cell via a flow channel, 17. The channel exiting the flow cell is split into two or more channels which lead to collection vessels for various products and waste. The direction of the eluent flow is controlled by a rotary valve, 3c, operatively attached to a feedback loop with at least one of the spectrophotometric detector or radiometric detector, 11, via a controller. The spectrophotometric source and detector are each attached to the analytical device via optical cables, 8. In a default setting, the waste line, 14a, should be the open path. Detection of the desired radiolabeled compound triggers the switching of the output from the waste line, 14a, to the product line (the fraction collector), 12a. When either the end of the desired fraction or the beginning of the next fraction is detected the valve, 3c, is switched to the appropriate position. The microfluidic advantage lies in the minimization of dead volume and cross-contamination of neighboring fractions.

One approach to integrating the spectrophotometric source and detector onto the analytical device is to connect them to the flow cell via fiber-optics or their equivalent. Such an arrangement also allows the source and the detector both to be placed outside the radioactivity shielding of the device, thereby minimizing the weight required for the radiation shield and protecting the electronics from radiation damage.

The spectrophotometric source/detector, for example, a UV source/detector, allows determination of chemical purity of the sample. For concomitant determination of radiochemical purity, and the detection of radioactive compounds (e.g. the desired product) in general, a radiation detector is placed underneath, on top of or both underneath and on top of the flow cell of the analytical device. Isolation of the desired radioactively labeled product takes place based on information from both detectors. By comparing the experimental data transmitted from the UV and/or radiometric detectors with standards, it is possible to determine the identity and purity of a particular fraction. For example, if there is a significant UV signal coinciding with the radiometric signal, the labeled product most likely is contaminated with a non-radioactive compound and therefore has a low specific activity.

When the analytical device is part of an automated instrument, the latter is programmed to receive a particular combination of UV and radio-signals to coordinate one or more valves for product collection. Since the fraction separation provided by the device of the present application is very precise, the arrangement presented in FIG. 1 may eliminate the need to follow the preparative HPLC column by an analytical column, making this a single-pass isolation/quality control device. Alternatively, a separate quality control device can originate from the final product valve, where aliquots (approximately 1 µL) can be drawn to assess different parameters of quality control (such as pH, chemical and radiochemical purity, solvent contamination, endotoxins, sterility, etc.) necessary for injectable dose validation.

In one embodiment of the present application, within the detection/isolation module are two regions: the detectors and the fraction collector, as shown in FIGS. 3A and 3B. In the detection region, the front and back of the module are used for attaching the fiber optic cables, 8, employed in optical absorbance detection while the top and bottom of the device are where the radiometric detector(s), 11, is attached. In the fraction collection region, an on-chip valve, 3c, switches between waste, 14a, and sample, 12a, based on the signal received by the controller from the radiometric detector(s), 11, and/or the spectrophotometric detectors. The on-chip valve, 3c, is designed to be driven electromechanically. Placing the detection and separation functionality into the same device assures precision in the fraction collection and minimizes the chance of inter-contamination between different fractions.

Figure 4:
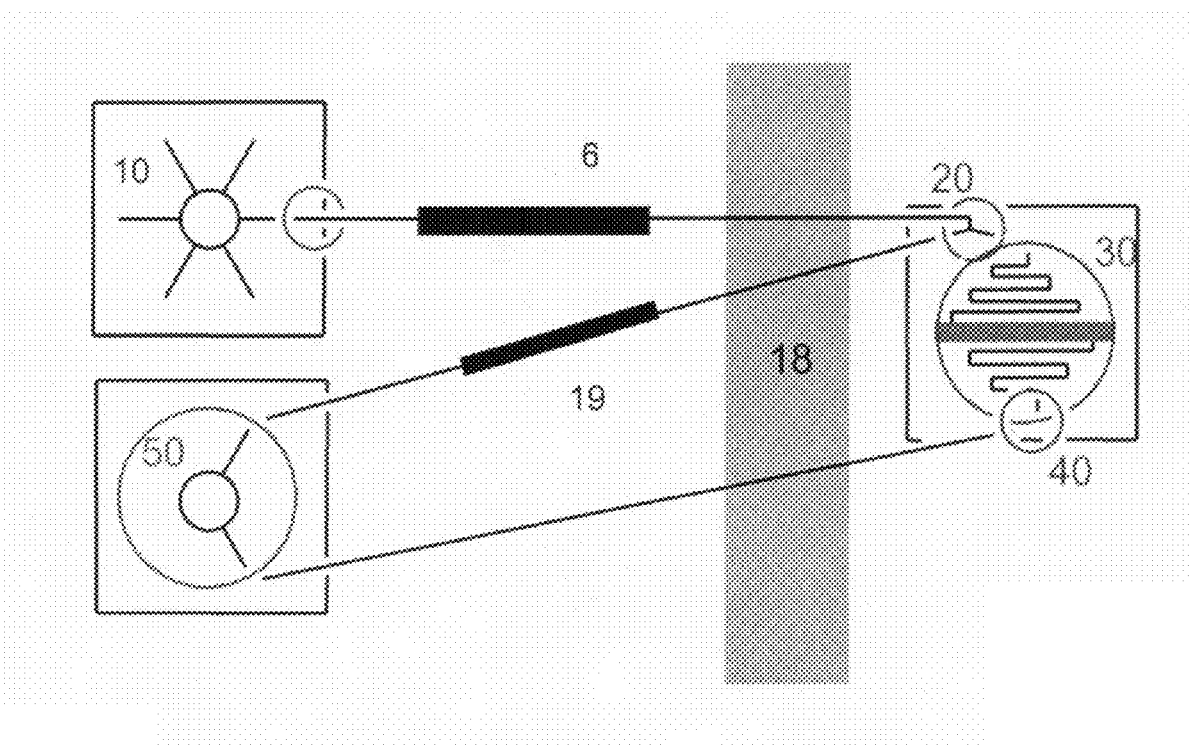
FIG. 4 is a schematic illustration of a set of microfluidic chips according to another embodiment disclosed in the present application in which the detection chip is separated from the synthesis and collection chips by a radiation shield.

As represented by FIG. 4, an alternate embodiment of the present application, collection chip, 50, can be separate from detection chip, 30, which is connected via flow channels to both collection chip, 50, and radio-synthesis chip, 10, but is shielded from those chips with a radiation shield, 18. In this example, the solution produced in radio-synthesis chip, 10, exits the chip, is purified during passage through an HPLC column, 6, of the type disclosed above, and enters the detection chip, 30, at the detector inlet valve, 20. The eluent from the HPLC column, 6, is analyzed in detection chip, 30, which is operatively attached to at least one of a radiation detector and a spectrophotometric source/detector pair. The eluent is then passed from the separation valve, 40, to the collection chip, 50, which is operatively attached to at least one of a waste collector, 14a, and a fraction collector, 12a. If the purity of a targeted fraction needs to be confirmed, then an aliquot of the fraction can be passed from the collection chip, 50, back to the detection chip, 30, via a flow channel that contains an analytical capillary column, 19. In such an example, after passage through the analytical column, 19, the detection chip, 30, can be used to assess the radiometric and/or chemical purity of the isolated sample. After this second passage through the detection chip, 30, the sample is passed back to the collection chip, 50, and can be isolated to a fraction collector, 12a. In one variation disclosed in the present application, the collection chip, 50, is replaced by a solvent removal system. Any pressure discrepancy between the devices and the chromatography columns shown in FIG. 4 can be overcome via placement of check valves.

Alternately, instead of sending the sample fraction from the collection chip, 50, back to the first detection chip, 30, a second detection chip can be employed. The second detection chip is in fluid communication with the collection chip, 50, via a flow channel containing an analytical column. The analytical column is used for further separation of the targeted fraction and the second detection chip is used to analyze the radiochemical and/or chemical purity of the sample.

Figure 5:
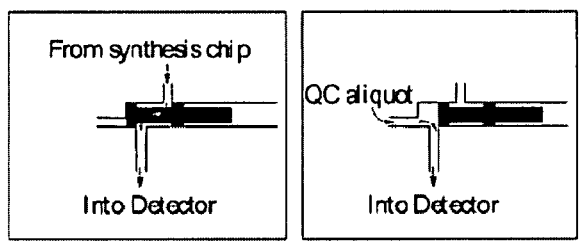
FIG. 5 is a close-up schematic of an alternate embodiment of the present application, in particular, one alternative for the operation of valves at the entrance and exit of a detection chip.
Figure 5:
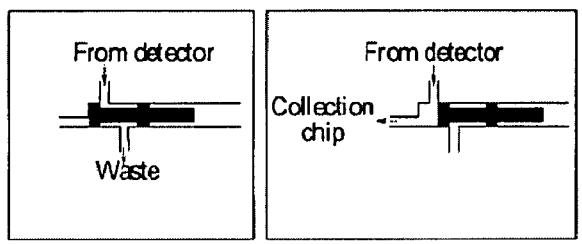
Figure 5:
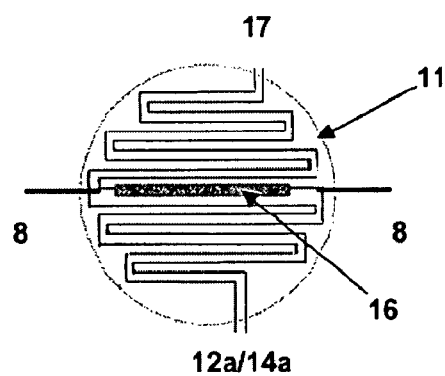

FIG. 5 provides a close-up schematic of the operation of the detection chip, 30. The length of the serpentine channel, stretching from the flow channel, 17, from the HPLC column, to the fraction/waste collectors, 12a/14a, can be varied to tune the sensitivity of the radiation detector, 11, which is attached to the bottom of the chip. The length of the flow cell, 16, which is part of the serpentine channel, can be varied to tune the spectrophotometric sensitivity. The spectrophotometric source/detector pair are attached to the detector chip, 30, via fiber optic cables, 8. As shown, the detector inlet valve, 20, allows the input to be switched between a preparative column and an analytical column attached thereto, utilizing the same detector for both product isolation and quality control testing. The separation valve, 40, directs the mobile phase to either waste, 14a, or desired fraction collection, 12a.

Figure 6:
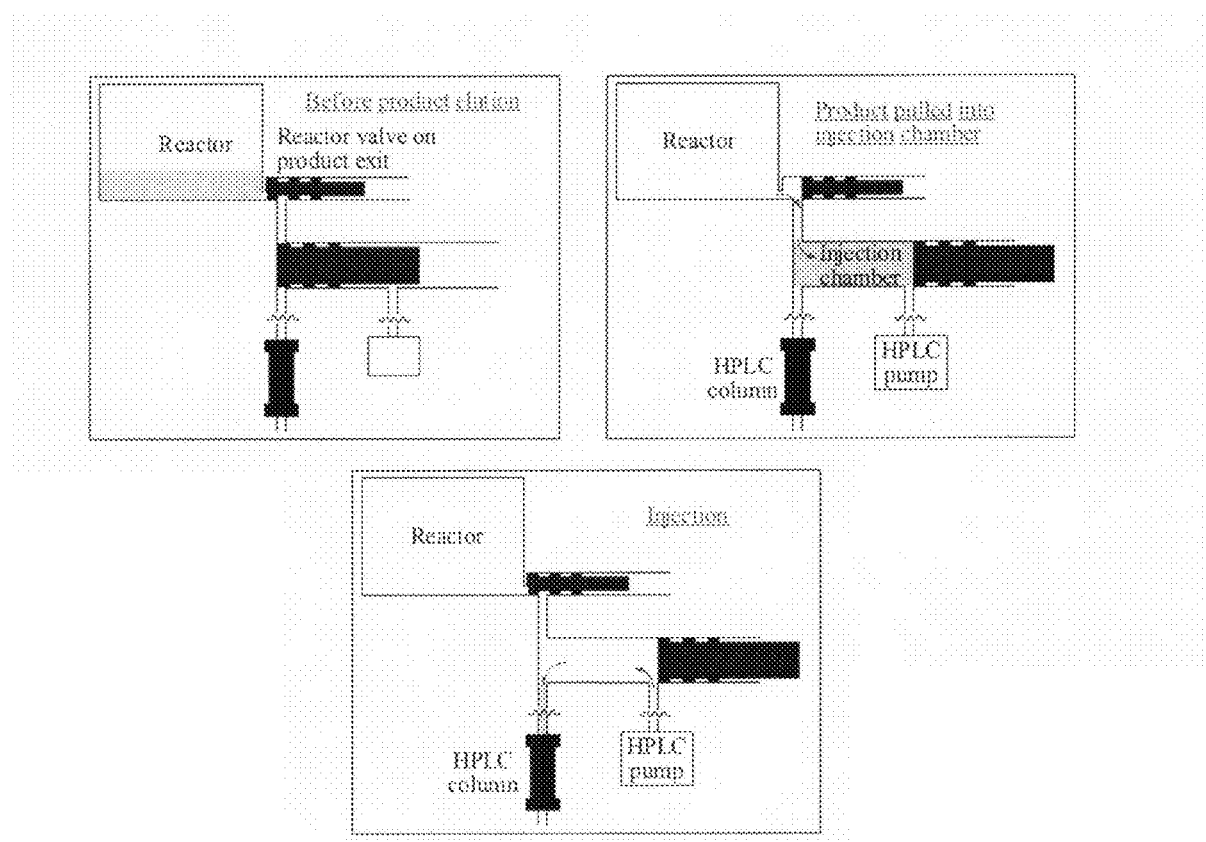
FIG. 6 is a schematic illustration according to one embodiment of the present application of the transfer of product from a radio-synthesis chip onto an HPLC column. This configuration is an alternative to direct injection from the synthesis chip onto the HPLC column, via a check valve or its equivalent.

As represented by FIG. 6, an alternate embodiment of the present application, a check valve between the radio-synthesis chip and the HPLC column as described in conjunction with FIG. 1 is not required. In this example, the solution is traveling on a single chip and thus has a smaller travel volume; transfer of the solution is controlled by plungers.

Figure 7:
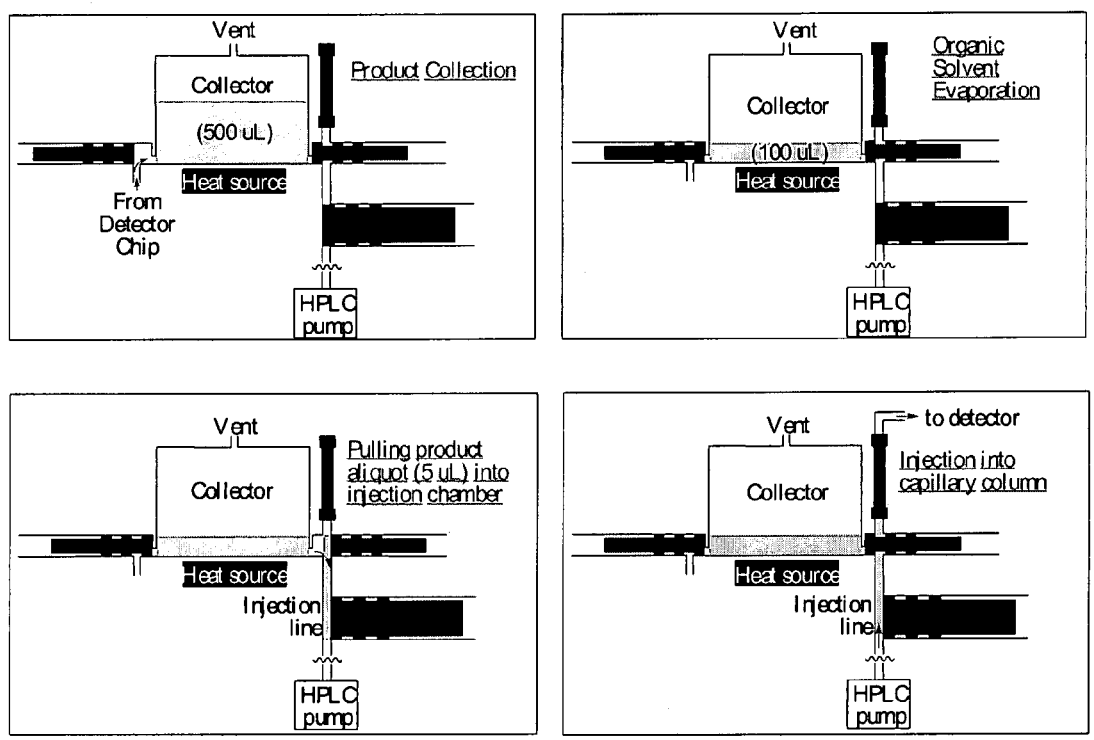
FIG. 7 is a close-up schematic according to one embodiment of the present application of the operation of a product collection, concentration, and quality control aliquoting chip. This collection chip can be used as an alternative to the solvent removal system described elsewhere in this application.

FIG. 7 discloses operation of plungers contained on the collection chip, 50. In particular, operation of the plungers can be configured to enable removal of organic solvent and transfer of a 5 µL aliquot as part of the secondary analytical system described herein.

One advantage of the systems disclosed in this application is that they enable the design of completely autonomous radio-synthesis modules, which perform radio-synthesis of PET or SPECT imaging agents inside the synthesis chip, followed directly by purification through the integrated HPLC column and chemical and radiochemical evaluation by the analytical device. Such an instrument can, for example, be used in a clinic rather than in a radio-pharmacy since it will not require specially-trained staff to handle any manual operation. In particular the systems described herein can be portable and do not require a hot cell (leaded cabinet), since each system can be configured with internal shielding which covers only the components that handle radiation rather covering than the entire system. The internal shielding is in addition to the shielding surrounding the analytical device, which enables improved determination of radiometric purity.

Other tests can be integrated on the analytical device or the secondary analytical system making the radio-synthesis instruments more user-friendly and operator-independent. Such tests can include, but are not limited to determination of pH, chemical and radiochemical purity, solvent contamination, endotoxins, and sterility, etc.

As described in more detail herein, in one embodiment of the present application, the microfluidics analytical device can be used an analytical tool used to test the purity of samples that have already gone through an HPLC purification step, optionally without use of valves to separate the solutions. Alternately, the detection chip described herein can be used for purity analysis, particularly evaluating the chemical and/or radiochemical purity of a sample. In another embodiment, an analytical device is used in tandem with the HPLC column, where the sample is analyzed continuously as it exits the column and the fractions are isolated in a more precise manner than in conventional purification.

The systems disclosed in this application not only simplify radio-synthesis and quality control, but also minimizes product loss, because they eliminate the need for removing a large portion of the product for external, macroscopic quality control. For example, a traditional radio-synthesis utilizes approximately 10 mCi of product for quality control purposes; 10 mCi is equivalent to one human dose. The microfluidics device of the present application will minimize or even eliminate this loss, making more product available for use in a patient.

In one embodiment, the radiochemical separation/purification system described herein features direct sample loading from a microfluidic synthetic device, which substantially minimizes sample loss and reduces time required for purification. Conventionally, once synthesis is completed in the synthesis device, the product is flushed out of the reactor into a crude product container. Entry into the chromatography column marks the beginning of the purification system. The purification/detection/isolation system described herein eliminates multiple transfers of the crude and pure samples that lead to material loss in conventional systems.

In another embodiment, direct loading of a sample prepared in a microfluidic radio-synthesis device onto the HPLC column is achieved through the addition of a check valve in the corresponding flow channel. The check valve employed in the systems disclosed herein allows liquid flow only in one direction and sustains the pressure generated by solvent pumps attached thereto. (See FIG. 1) In one aspect, the microfluidic system of the present application does not require an injection loop and the HPLC column is not preceded by either a sample loop or a trap column; the HPLC column is in direct fluid communication with the check valve. That is, the radiochemical separation/purification system described herein eliminates the sample loop and additional trap column that generally precede chromatography columns in conventional systems and lead to material loss; this elimination makes the separation both efficient and independent of the sample volume. Direct loading also simplifies the system design by eliminating the high pressure valve generally employed in conventional systems. In one variation, the HPLC column employed is a monolith column. Conventional systems utilizing monolith columns generally require an injection loop or its fixed volume equivalent, however the system design described herein does not. The monolith columns as described in the microfluidic system of the present application yield much lower back pressure than traditional packed columns and facilitate loading of the column from the synthesis chip without the requirement of an injection loop or sample loop.

Generally, a high pressure liquid chromatography column requires a sample loop to define the sample size loaded onto the separation column. Unfortunately, the sample loop may lead to unnecessary sample loss. In the system disclosed herein, a step change in solvent composition is applied, which retains or can even improve the HPLC separation efficiency. The step change can be fulfilled by switching between different solvents. The different solvents can be input into the system using at least one pump in fluid communication with the check valve described above. Alternately, solvents of varying hydrophobicity can be used with one or more pumps. In some examples, it would be appropriate for combinations of two or more solvents to be used to achieve separation of the targeted product from its side products. Control of the pump (s) to yield such solvent combinations can be achieved in an automated fashion, optionally employing a feedback loop incorporating data collected from one or more detectors attached to the analytical device.

As represented in FIG. 1, the system can be configured with more than one solvent source. Each solvent source can be controlled by a unique solvent pump or alternately, all of the solvent sources can be operated by a single solvent pump. To fully take advantage of the system in an automated mode, the delivery of each solvent, or combination thereof, is controlled by a controller, based on a feedback loop responding to data collected by the one or more detectors at the analytical device. For example, in the purification and isolation of $^{18}$F-FLT, the sample from the microfluidic radio-synthesis device is loaded onto the HPLC column. The column is first washed with water, thereby carrying the hydrophilic impurities through the column; the column is then washed with a more hydrophobic solvent, 8% ethanol, thereby eluting the targeted fraction.

In one embodiment, the targeted fraction is collected in a sample collection vial and is held in a vial holder or an array of vials; the vial is temperature controlled and can be furnished with an inert gas stream. The sample vial is heated and has an inert gas flow at the overhead of the solvent level. In a matter of minutes, the combination of high temperature, usually at a temperature below which the radiolabeled compound is stable, and the flowing gas, usually nitrogen gas, efficiently removes the organic solvent in the fraction. Generally the temperature can be held at up to about 120° C., alternately up to about 100° C. The pressure of the flowing gas is generally controlled between about 20 and about 50 psi, alternately, the pressure of the gas is between about 15 psi and 35 psi. A trap is placed in fluid communication with the sample vial at the exit to absorb or condense the solvent vapor and to prevent any radioactive material from entering the environment. During sample collection high temperature and gas flow substantially reduce the content of organic solvent in the sample.

In general, drug products to be used in vivo must have low organic solvent content. By controlling the temperature and the nitrogen flow of the solvent removal system, one can tune the system to remove various solvents and meet FDA requirements for acceptable solvent contamination of injectable products. The system as described is capable of taking the desired radiochemical product out of a crude reaction mixture and yielding it in a form in which it can be injected into a patient, optionally after filtration through a sterility filter, such as a Millex filter or a Pall filter. Verification of in vivo applicability (and meeting FDA requirements) of the product can be verified by an automated quality control system before the product is injected into a patient.

Representative Examples Using the Configuration Shown in FIG. 1:

$^{18}$F-FLT was prepared in a microfluidic radio-synthesis device; then the radiolabeled compound was purified using an HPLC column and isolated using a microfluidic analytical device attached thereto. A radiolabeled compound can be prepared, purified and isolated in a synthesis/purification/isolation system configured in FIG. 1.

The HPLC column employed was a monolithic C18 semi-preparative column purchased from Phenomenex; the optical fibers were connected to a UV source/detector and the radiometric detector was attached to the top of the analytical device. The radiometric detector was a compact detector probe, which consisted of a 1-cm$^3$ CsI(Tl) scintillation crystal and a 1-cm$^2$ silicon PIN diode. The heater at the fraction collector was a 1" by 3" 10 W thermoelectric unit which warmed the sides and bottom of the fraction collector. Nitrogen was used as the inert gas, the flow of which was controlled with a gas flow regulator. The first solvent was water and the second solvent was 8% ethanol. The HPLC column was primed with pure water by flushing 4 mL/min for 4 minutes.

Figure 8A:
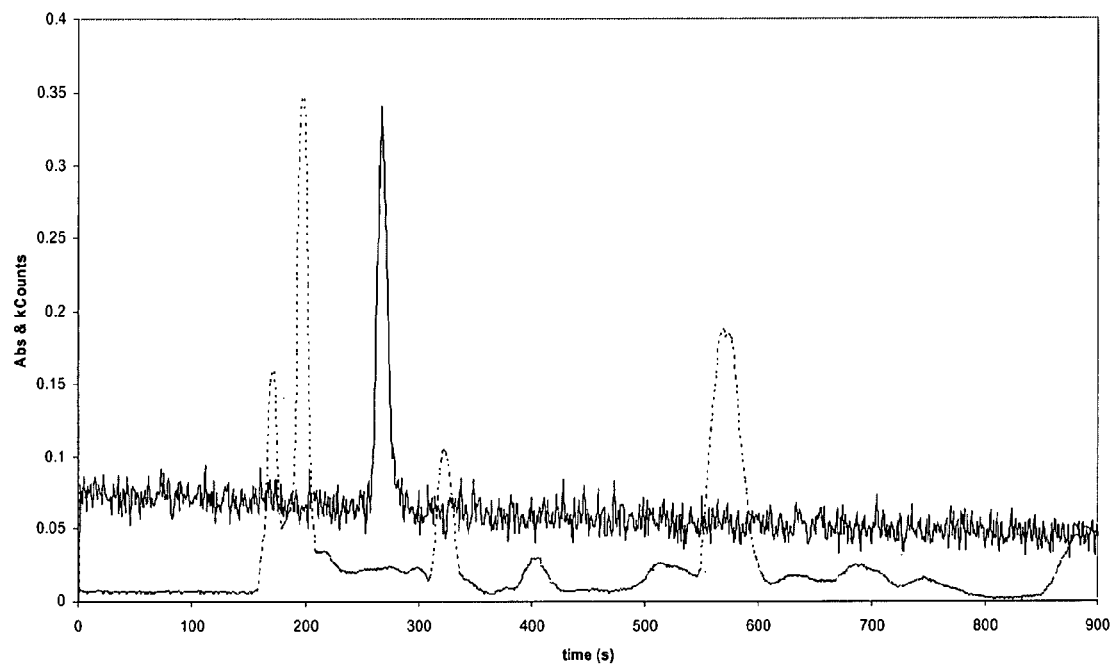
FIG. 8A is a chromatogram of the UV absorbance and radiation signal from $^{18}$F-labeled 3'-deoxy-3'-fluorothymidine ($^{18}$F-FLT) isolated by an automated test system described herein.

Synthesis of $^{18}$F-FLT was completed in the radio-synthesis device. The entire volume of the reaction mixture and a rinse volume (0.5-1 mL water) were then transferred to an HPLC column. The flow rate in the purification process was held at about 4 mL/min. The back pressure at this flow rate was lower than 800 psi. A water 'pre-wash' of the loaded chromatography column removed water-soluble impurities, such as $^{18}$F-ions, and improved the peak shape for the subsequent separation/purification process (see FIG. 8A). A second, more hydrophobic solvent, 8% ethanol, was then provided. This solvent change eliminated the need to pass either purified or crude sample through any fluoride trapping material such as ion exchange or alumina. As the flow rate was held to 4 mL/min and the detection window parameters are 0.02" ID and 0.5-1 cm, the residence time of the sample band in the detection zone was estimated to be 15-30 ms.

Based on a targeted retention time (equal or less than 5 minutes), and as determined by the measurement of radiometric purity, $^{18}$F-FLT having greater than 95% purity was isolated in a 4 mL glass vial. The vial was heated at about 100°

Figure 8B:
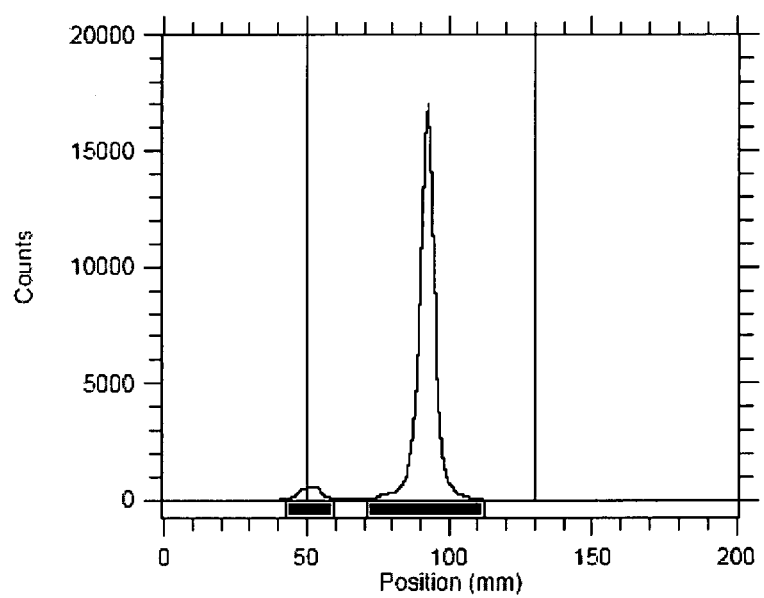
FIG. 8B is a radio-TLC trace obtained from $^{18}$F-FLT isolated by an automated test system described herein.
Figure 9A:
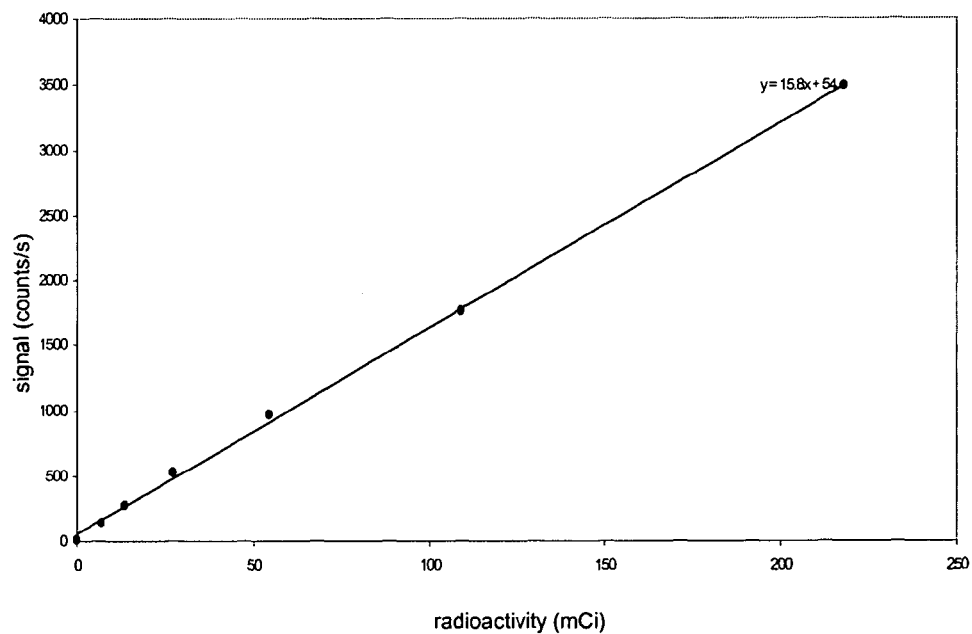
FIG. 9A is a calibration curve based on the detection of $^{18}$F-fluorine using a silicon P-type/intrinsic/N-type ("PIN")-based gamma probe.
Figure 9B:
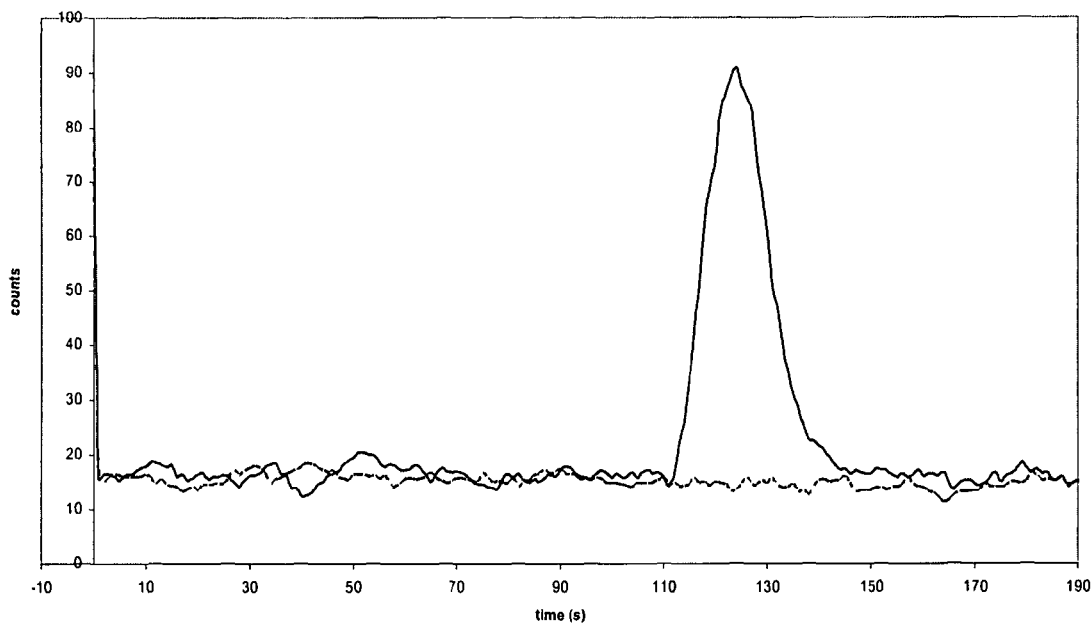
FIG. 9B is a graph showing a 6.8 µCi peak from an $^{18}$F-fluorine sample and the data from a blank. A limit of detection of 0.15 µCi has been demonstrated in this system.

C. via the heater and nitrogen was allowed to flow over the sample. A 1 mL 8% ethanol solution was reduced to less than half its original volume in 5 minutes. Purification and isolation were also tested in an automated isolation mode and confirmed successfully with $^{18}$F-FLT isolation, as represented by the radio-TLC shown in FIG. 8B. The process disclosed herein generally took less than 10 minutes.

All references cited herein are incorporated by reference as if each had been individually incorporated. The embodiments illustrated and discussed in this specification are intended only to teach those skilled in the art the best way known to the inventors to make and use the invention. Figures are not drawn to scale. No attempt is made to show structural details of the present application in more detail than may be necessary for a fundamental understanding of the invention.

It should be noted that features of one embodiment may be employed with other embodiments as the skilled artisan would recognize, even if not explicitly stated herein. Descriptions of well-known components and processing techniques may be omitted so as to not unnecessarily obscure the embodiments of the invention. In describing embodiments of the invention, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed:

1. A system for manipulating a radiolabeled compound-containing reaction mixture, the system comprising:
   i) a microfluidic analytical device comprising a microfluidic detection flow channel having an inlet and an outlet;
   ii) a first radiometric detector coupled to the top of the detection flow channel; and a second radiometric detectors coupled to the bottom of to the detection flow channel, for generating a signal corresponding to detection of the radiolabel in the detection flow channel, wherein said signal is registered simultaneously by both detectors, wherein the first and the second detectors are both operatively attached to a controller, the controller is configured so that any radiation signal not simultaneously received by both detectors is excluded from processing;
   iii) a spectrophotometric source for providing light to the detection flow channel;
   iv) a spectrophotometric detector for generating a spectrophotometric signal corresponding to detection of light from the detection flow channel to determine chemical identity and purity of the sample in the detection flow channel; and
   v) a high pressure liquid chromatography column onto which the reaction mixture can be loaded, the column having an inlet and an outlet, the inlet of the column being configured to receive the reaction mixture, and the outlet of the column being connected in fluid communication with the inlet of the detection flow channel of the device, wherein the column is selected such that the column can separate and purify the radiolabeled compound from the reaction mixture containing radiolabeled and non radiolabeled impurities;
   whereby when fluid containing the radiolabeled compound flows from the column into the detection flow channel, the radiometric detectors generate the signal and the spectrophotometric detector generates a spectrophotometric signal substantially simultaneously corresponding to the radiolabeled compound.

2. The system of claim 1, wherein the analytical device further defines a waste channel and a sample channel having an inlet and an outlet, and wherein the device further comprises a first microfluidic valve that is actuatable between
   a) a sample position fluidly connecting the detection flow channel and the inlet of the sample channel and
   b) a waste position fluidly connecting the detection flow channel and the waste channel.

3. The system of claim 2, wherein the first micro fluidic valve is operatively connected with at least one radiometric detector, whereby occurrence of both the spectrophotometric signal and at least one radiometric corresponding to the radiolabeled compound actuates the first microfluidic valve into the sample position.

4. The system of claim 2, wherein the outlet of the sample channel is fluidly connected with a sample reservoir.

5. The system of claim 3, wherein the sample reservoir is fluidly connected with the detection flow channel by way of a second microfluidic valve that is actuatable between
   a) an open position fluidly connecting the sample reservoir and the detection flow channel and
   b) a closed position in which the sample reservoir and the detection flow channel are not fluidly connected,
   whereby a fluid in the sample reservoir can be transferred to the detection flow channel when the second microfluidic valve is in the open position.

6. The system of claim 4, further comprising a radiation shield interposed between the sample reservoir and at least one radiometric detector.

7. The system of claim 1, wherein the substrate further defines a waste channel and a sample channel having an inlet and an outlet, and wherein the device further comprises a first microfluidic valve that is operatively connected with the controller and that is actuatable between
   a) a sample position fluidly connecting the detection flow channel and the inlet of the sample channel and
   b) a waste position fluidly connecting the detection flow channel and the waste channel.

8. The system of claim 1, wherein the spectrophotometric source provides light to the detection flow channel via a first fiber optic cable and wherein the spectrophotometric detector detects light from the detection flow channel via a second fiber optic cable.

9. The system of claim 1, wherein the spectrophotometric source provides UV light to the detection flow channel.

10. The system of claim 9, wherein the spectrophotometric detector detects UV light from the detection flow channel.

11. The system of claim 1, wherein the analytical device further defines a waste channel and a sample channel having an inlet and an outlet, and wherein the device further comprises a first microfluidic valve that is actuatable, by a controller operatively connected with the spectrophotometric detector, between
    a) a sample position fluidly connecting the detection flow channel and the inlet of the sample channel and
    b) a waste position fluidly connecting the detection flow channel and the waste channel.

12. The system of claim 1, further comprising a fraction collector actuatable by the spectrophotometric signal and the radiometric signal corresponding to the radiolabeled compound.

13. The system of claim 12, further comprising a sample collection vial that is placed in fluid communication with the outlet of the detection flow channel when the fraction collector is actuated.

14. The system of claim 13, wherein the vial has a solvent removal system associated therewith for evaporating solvent from the vial.

15. The system of claim 1, wherein the volume of the detection flow channel is from approximately 1 to approximately 10 microliters.

16. The system of claim 15, wherein the volume of the detection flow cell is about 1 microliter.

17. The system of claim 1, further comprising a check valve fluidly connected with the inlet of the column.

18. The system of claim 1, further comprising a radiation shield interposed between the column and at least one radiometric detector.

19. The system of claim 1, further comprising a microfluidic radio-synthesis device coupled with the inlet of the column.

20. A method of manipulating a radiolabeled compound-containing reaction mixture, the method comprising:
  i) passing the reaction mixture through a system comprising
    a) a high pressure liquid chromatography column selected such that the column can separate and purify the radiolabeled compound from the reaction mixture containing radiolabeled and non radiolabeled impurities, the column having an inlet and an outlet, the inlet of the column being configured to receive the reaction mixture, and the outlet of the column being connected in fluid communication with the inlet of the detection flow channel of
    b) a microfluidic analytical device comprising a microfluidic detection flow channel having an inlet and an outlet; the device having coupled thereto
      1) a first radiometric detector coupled to the top of the detector flow channel and a second radiometric detectors coupled to the bottom of the detection flow channel, for generating a signal corresponding to detection of the radiolabel in the detection flow channel, wherein said signal is registered simultaneously by both detectors; and wherein the first and the second detectors are both operatively attached to a controller, the controller is configured so that any radiation signal not simultaneously received by both detectors is excluded from processing; and wherein the first and second radiometric detectors are both operatively attached to a controller, and the controller is configured so that any radiation signal not simultaneously received by both detectors is excluded from processing;
      2) a spectrophotometric source for providing light to the detection flow channel; and
      3) a spectrophotometric detector for generating a spectrophotometric signal corresponding to detection of light from the detection flow; and
  ii) collecting a sample from the outlet of the detection flow channel when a spectrophotometric signal and the radiometric signal corresponding to the radiolabeled compound occur substantially simultaneously,
whereby the collected sample contains the radiolabeled compound.

21. The method of claim 20, wherein the substrate further defines a waste channel and a sample channel having an inlet and an outlet, and wherein the device further comprises a first microfluidic valve that is actuatable between
  I) a sample position fluidly connecting the detection flow channel and the inlet of the sample channel and
  II) a waste position fluidly connecting the detection flow channel and the waste channel, wherein the sample is collected by way of the sample channel with the first microfluidic valve in the sample position.

22. The method of claim 20, wherein the first microfluidic valve is operatively connected with at least one radiometric detector and wherein the first microfluidic valve is actuated into the sample position by occurrence of at least one radiometric signal.

23. The method of claim 20, wherein the sample is collected in a sample reservoir fluidly connected with the outlet of the sample channel.

24. The method of claim 23, wherein the sample reservoir is fluidly connected with the detection flow channel by way of a second microfluidic valve that is actuatable between
  I) an open position fluidly connecting the sample reservoir and the detection flow channel and
  II) a closed position in which the sample reservoir and the detection flow channel are not fluidly connected,
the method further comprising actuating the second microfluidic valve into the open position and transferring an aliquot of the sample from the sample reservoir to the detection flow channel.

25. The method of claim 20, wherein the substrate further defines a waste channel and a sample channel having an inlet and an outlet, and wherein the device further comprises a first microfluidic valve that is actuatable, by a controller operatively connected with each of the first and second radiometric detectors, between
  I) a sample position fluidly connecting the detection flow channel and the inlet of the sample channel and
  II) a waste position fluidly connecting the detection flow channel and the waste channel.

26. The method of claim 20, wherein light is provided to the detection flow channel from the spectrophotometric source via a first fiber optic cable and wherein light from the detection flow channel is provided to the spectrophotometric detector via a second fiber optic cable.

27. The method of claim 20, wherein the spectrophotometric source provides UV light to the detection flow channel.

28. The method of claim 27, wherein the spectrophotometric detector detects UV light from the detection flow channel.

29. The method of claim 20, wherein the controller actuates the first microfluidic valve when
  A) the first signal occurs,
  B) the second signal occurs, and
  C) the spectrophotometric signal corresponds to the compound.

30. The method of claim 20, further comprising evaporating solvent from the collected sample.

31. The method of claim 20, wherein the volume of the detection flow channel is from approximately 1 to approximately 10 microliters.

32. The system of claim 1, wherein the detection flow channel is a serpentine channel.

33. The system of claim 32, wherein a flow cell is a part of the serpentine channel.

34. The system of claim 32, wherein length of the serpentine channel is varied to tune the sensitivity of the radiometric detector.

35. The system of claim 33, wherein length of the flow cell is varied to tune the spectrophotometric sensitivity.

36. The system of claim 1, wherein the high pressure liquid chromatography column is a preparative column.

37. The system of claim 1, wherein the high pressure liquid chromatography column is an analytical column.

38. The system of claim 1, wherein additional radiometric noise is removed from the analysis when any radiation signal not simultaneously received by both radiometric detectors is excluded from processing.

39. The system of claim 1, wherein the system is automated.

40. The system of claim 1, wherein the system is self-contained.

41. The system of claim 1, wherein the system features an automated in-line purification and isolation of the radiolabeled compound.

42. The system of claim 41, wherein the system further includes microfluidic radio-synthesis device.

* * * * *